United States Patent [19]

Feuer

[11] Patent Number: 5,445,178

[45] Date of Patent: Aug. 29, 1995

[54] SOIL MOISTURE SENSOR

[76] Inventor: Lenny Feuer, 16216 Brooks Rd., Grass Valley, Calif. 95945-8816

[21] Appl. No.: 198,433

[22] Filed: Feb. 18, 1994

[51] Int. Cl.$^6$ .................................... A01G 25/16
[52] U.S. Cl. .................................... 137/1; 137/78.3; 239/64
[58] Field of Search .................. 137/78.3, 1; 239/64, 239/70, 69

[56] References Cited

U.S. PATENT DOCUMENTS

| | | | |
|---|---|---|---|
| 3,771,548 | 11/1973 | Rauchwerger | 137/78.3 |
| 4,548,225 | 10/1985 | Busalacchi | 137/78.3 |
| 4,657,039 | 4/1987 | Birdey et al. | 137/78.3 |
| 4,683,904 | 8/1987 | Iltis | 137/78.3 |
| 4,785,843 | 11/1988 | Nicholson | 137/78.3 |
| 4,850,386 | 7/1989 | Bireley | 137/78.3 |
| 4,852,802 | 8/1989 | Iggulden et al. | 137/78.3 |
| 4,892,113 | 1/1990 | Fattahi | 137/78.3 |
| 4,936,333 | 6/1990 | Bireley | 137/78.3 |
| 4,941,501 | 7/1990 | Bireley | 137/78.3 |

*Primary Examiner*—A. Michael Chambers
*Attorney, Agent, or Firm*—Spensley Horn Jubas & Lubitz

[57] ABSTRACT

Moisture sensor devices, systems and methods of making and using the same employ a pair of elongated, probe-like, conductive sensor elements, coupled as part of an LC oscillator circuit. The use of an LC oscillator circuit can minimize adverse effects of conductivity variances in the medium being monitored, because the resistance of the medium (and, thus, the medium's conductivity) has minimal or no effect on the resonant frequency of an LC oscillator circuit. An LC oscillator circuit of suitable stability for moisture sensing applications includes first and second comparators connected such that the output of the first comparator is coupled to the inverting input of the second comparator. An inductor is coupled between the output and inverting input of the first comparator and a capacitance C is provided between the output of the second comparator and the inverting input of the first comparator. The capacitance C is composed primarily of the capacitance value provided by the pair of probe-like sensor elements and the dielectric constant of the medium in which the probe-like sensor elements are disposed. The capacitance is averaged over the length of the probe-like sensor elements.

28 Claims, 7 Drawing Sheets

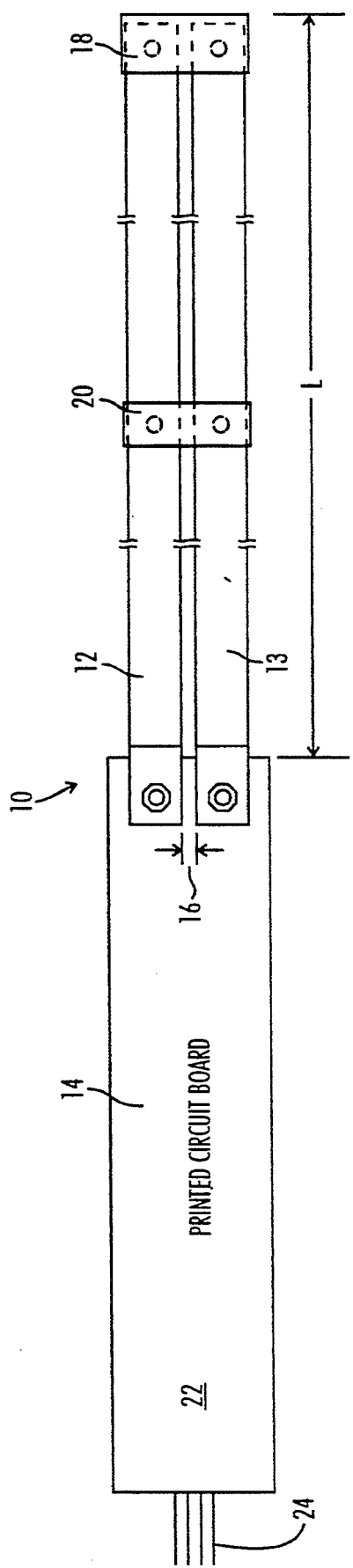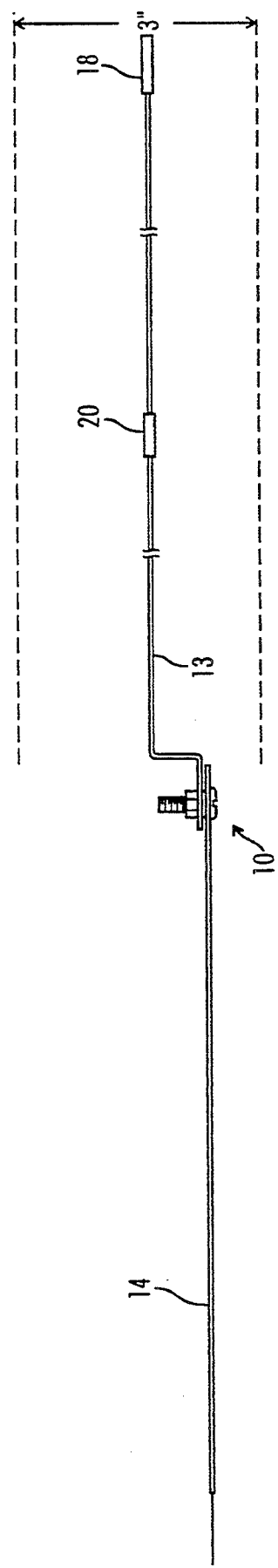
FIG. 1
FIG. 2

SOIL MOISTURE SENSOR

BACKGROUND OF THE INVENTION

1. Field of the Invention

The present invention relates generally to moisture sensor devices, systems and methods of making and using the same and, in particular embodiments, to a moisture sensor device, system and method for sensing the moisture content of soil or other suitable medium.

2. Related Art

It is often desirable to detect the moisture content of a granular, particulate, fine or powdery medium. For example, in agriculture, it is often desirable to detect the moisture content of the soil in a region, so that irrigation or drainage systems can be controlled in accordance with the sensed moisture content. Soil moisture detection is also desirable for other purposes, e.g., for monitoring and evaluating the soil condition in construction sites, landscaped sites, mining operations, forest areas, flood control areas, or bio-remediation areas, such as areas in which liquid or other contaminant has spilled.

The ability to determine the moisture content of granular, particulate, fine or powdery media is also important in many other applications, such as cement or plaster making systems, gravel or brick processing systems, mined material moving or processing systems and food processing or handling systems, to name just a few. Another application for moisture content monitoring relates to the monitoring of the moisture content of certain water absorbing substrates, such as mushroom substrates, or other agricultural or laboratory substrates. As the demand for agricultural products increases and as the demand for higher quality products made from granular, particulate, fine or powdery media, or made with a moisture absorbing media increases, so does the demand for high quality moisture detection systems. Accurate moisture detection systems can dramatically increase the ability to meet the increasing market demands for these products. In addition, accurate moisture detection systems can increase the manufacturing efficiency and quality of such products.

For low dielectric media (such as soil), it has been recognized that moisture content affects the overall dielectric constant of such media to a detectable degree. For example, water has a relatively high dielectric constant of 80, while dry soil typically has a much lower dielectric constant of approximately 5 or 6. The water content in soil is, thus, generally a major contributor to the overall dielectric constant of the soil. An increase in the moisture content of soil will generally result in an increase in the dielectric constant of the soil. The same is typically true with many other low dielectric granular, particulate, fine or powder substances or media.

Accordingly, moisture sensors have been developed for reacting to the dielectric property of the medium being monitored. Moisture sensors of contemporary design typically employ a parallel plate capacitor configured to be immersed or embedded in the medium so that a portion of the medium becomes embedded between the parallel plates and functions as a dielectric between the plates. The capacitance provided by such a capacitor is used as part of an RC oscillator circuit having an oscillation frequency which varies with changes in the dielectric property of the small portion of the medium between the plates. The frequency of the oscillator circuit is used as an indicator of the moisture content of the medium.

However, the conductivity properties of the medium tends to adversely affect the ability of such RC oscillator-based systems to accurately indicate the moisture content of the medium. The conductivity of a medium tends to affect the oscillation frequency of RC-oscillator circuits. With such systems, it may be difficult, if not impossible, to separate the affect of the medium's conductivity properties from the affect of the medium's dielectric properties. This can be especially problematic where the volume of the medium to be monitored is non-uniform with respect to conductivity. Typically, soil is non-uniform with respect to many parameters, such as moisture retention, density and percentages of particular constituent materials and elements that form the soil. Such non-uniformities tend to result in non-uniform conductivity characteristics over a given volume of soil.

For example, if the medium to be monitored is soil in an agriculture area, the soil may contain various additive components, such as fertilizers, PH buffers, naturally occurring salts, and the like. Also, the salinity of the soil may be relatively high or may vary over a given volume. In addition, due to the general nature of typical agriculture soils, the soil in the agriculture area may contain portions of relatively high moisture concentration and portions of relatively low moisture concentration. Such soil additives, salinity and moisture concentration variances tend to result in variances in the conductivity of the soil and, thus, variances in the oscillation frequency of such prior RC oscillator circuits. In this regard, placement of a soil moisture sensor in certain portions of the agriculture area (e.g., portions having high or low moisture concentrations, portions having high or low concentrations of conductive additives and/or portions having high or low salinity concentrations relative to the entire agriculture area) may provide an inaccurate indication of the moisture concentration in the agriculture area.

Prior systems have employed a dielectric coating (such as an anodization) on one or both of the parallel plates in an attempt to alleviate the adverse effects of soil conductivity. However, such dielectric coatings also tend to adversely affect the accuracy of the circuit to react to the dielectric constant of the soil. Moreover, it has been found that such dielectric coatings are typically ineffective for alleviating the adverse effects of soil conductivity.

Examples of moisture sensors proposed for detection of moisture in soil are described in U.S. Pat. No. 4,657,039 to Bireley, et al. (issued Apr. 14, 1987, U.S. Pat. No. 4,850,386 to Bireley (issued Jul. 25, 1989), U.S. Pat. No. 4,936,333 to Bireley (issued Jun. 26, 1990) and U.S. Pat. No. 4,941,501 to Bireley (issued Jul. 17, 1990), each of which are incorporated herein by reference. The devices described in the above-cited Bireley and Bireley et al patents each employ a multi-vibrator type RC oscillation circuit that reacts to the impedance between a pair of electrodes located in the soil and a variable capacitance having a value dependent upon the moisture content of the soil being monitored. However, as noted above, RC oscillation circuits are highly susceptible to the conductivity of the medium being monitored. Bireley's variable capacitance signal is provided by a pair of plate-type electrodes coated with a dielectric material, as discussed above. However, as noted above, dielectric coating on sensor electrodes can adversely affect the accuracy of sensor (as well as increasing the manufacturing complexity and cost).

SUMMARY OF THE DISCLOSURE

The present invention relates generally to moisture sensor devices, systems and methods of making and using the same which obviates, for practical purposes, the above noted drawbacks of the prior art. Moisture sensor devices according to preferred embodiments of the present invention comprise a pair of elongated, probe-like, conductive sensor elements, coupled as part of an LC oscillator circuit.

The present inventor has recognized that the use of an LC oscillator circuit can minimize the above-noted adverse effects of conductivity variances in the medium being monitored. In particular, because the resonant frequency of RC type oscillator circuits depend upon the resistance value R as well as the capacitance value C, the resistance (and, thus, conductivity) of the medium tends to affect the oscillation frequency of the circuit. However, the resistance of the medium (and, thus, the medium's conductivity) has minimal or no effect on the resonant frequency of an LC oscillator circuit.

According to a preferred embodiment of the invention, an LC oscillator circuit of suitable stability for moisture sensing applications comprises first and second comparators connected such that the output of the first comparator is coupled to the inverting input of the second comparator. A voltage signal (e.g., 2.5 V) is provided to the noninverting input of each comparator. An inductor is coupled between the output and inverting input of the first comparator and a capacitance C is provided between the output of the second comparator and the inverting input of the first comparator. The capacitance C is composed primarily of the capacitance value provided by the pair of probe-like sensor elements and the dielectric constant of the medium in which the probe-like sensor elements are disposed.

In operation, the probe-like sensor elements are installed in a volume of the medium to be monitored (e.g., by pushing or burying the probe-like elements in the medium). The sensor elements function as capacitor plates, while the medium between and around the sensor elements function as the capacitor dielectric. The capacitance C provided by the sensor elements and the medium is, therefore, dependent on the dielectric constant of the medium. The resonant frequency of the LC oscillator circuit is dependent, in part, on the value of the capacitance C and, therefore, on the dielectric constant of the medium.

The output signal of the LC oscillator circuit is converted to an analog signal having an amplitude dependent on the frequency of the oscillator circuit output signal and, thus, is dependent (and representative of) the dielectric constant of the medium. Because the conductivity of the medium has minimal effect on the resonant frequency of the LC oscillator circuit, the medium conductivity also has minimal effect on the amplitude of the analog signal. As a result, the amplitude of the analog signal provides a highly accurate indication of the dielectric constant of the medium (and, thus, the moisture content of the medium).

Also, the inventor has recognized that elongated, conductive, probe-like sensor elements provide a capacitance value determined by the average capacitance over the length of the elements. Thus, according to preferred embodiments of the present invention, a suitable probe length is chosen to extend a suitable distance within the medium to be monitored, such that variances in the moisture content of the medium along the length of the probes will be compensated for by averaging of the capacitance value over the length of the probes. In preferred embodiments, the length of the probes is approximately 29 inches.

These and other objects of the present invention will become more readily appreciated and understood from a consideration of the following detailed description of the preferred embodiments when taken together with the accompanying drawings, in which:

BRIEF DESCRIPTION OF THE DRAWINGS

FIG. 1 is a top view of a soil moisture sensor in accordance with a preferred embodiment of the present invention.

FIG. 2 is a side view of the soil moisture sensor of FIG. 1.

DETAILED DESCRIPTION OF THE PREFERRED EMBODIMENTS

Figure 3:
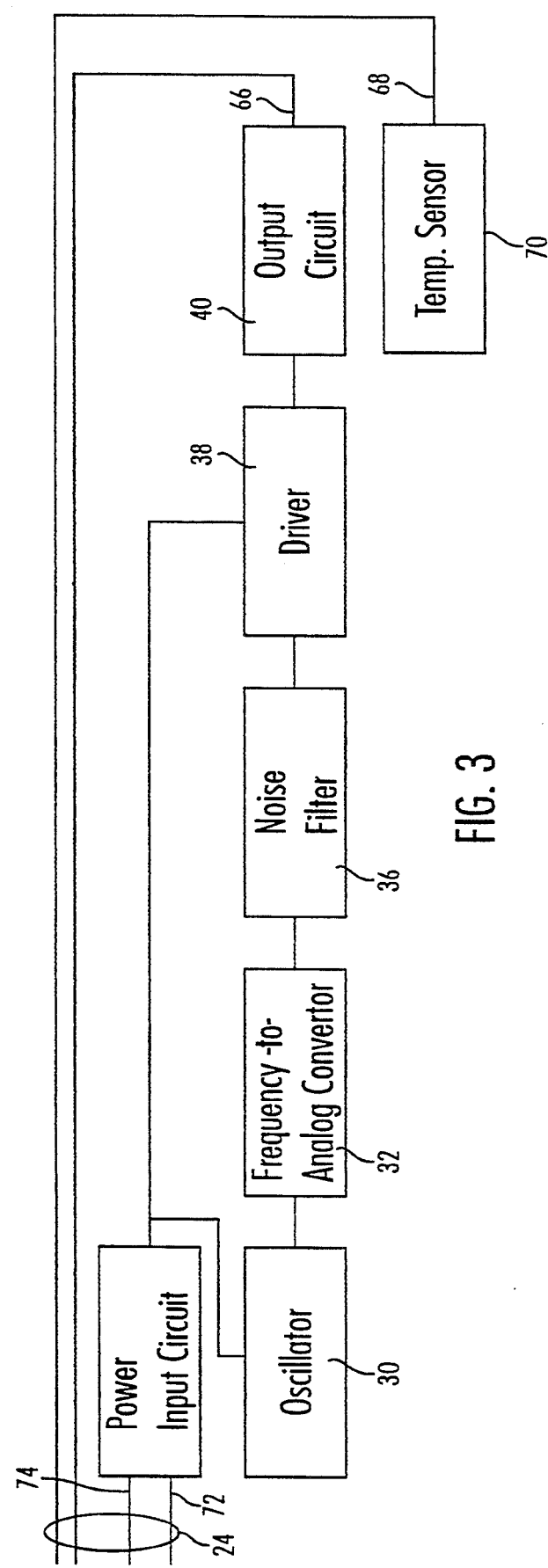
FIG. 3 is a block diagram of a preferred embodiment of the electrical circuit on the printed circuit board of the soil moisture sensor of FIG. 1.
Figure 4A:
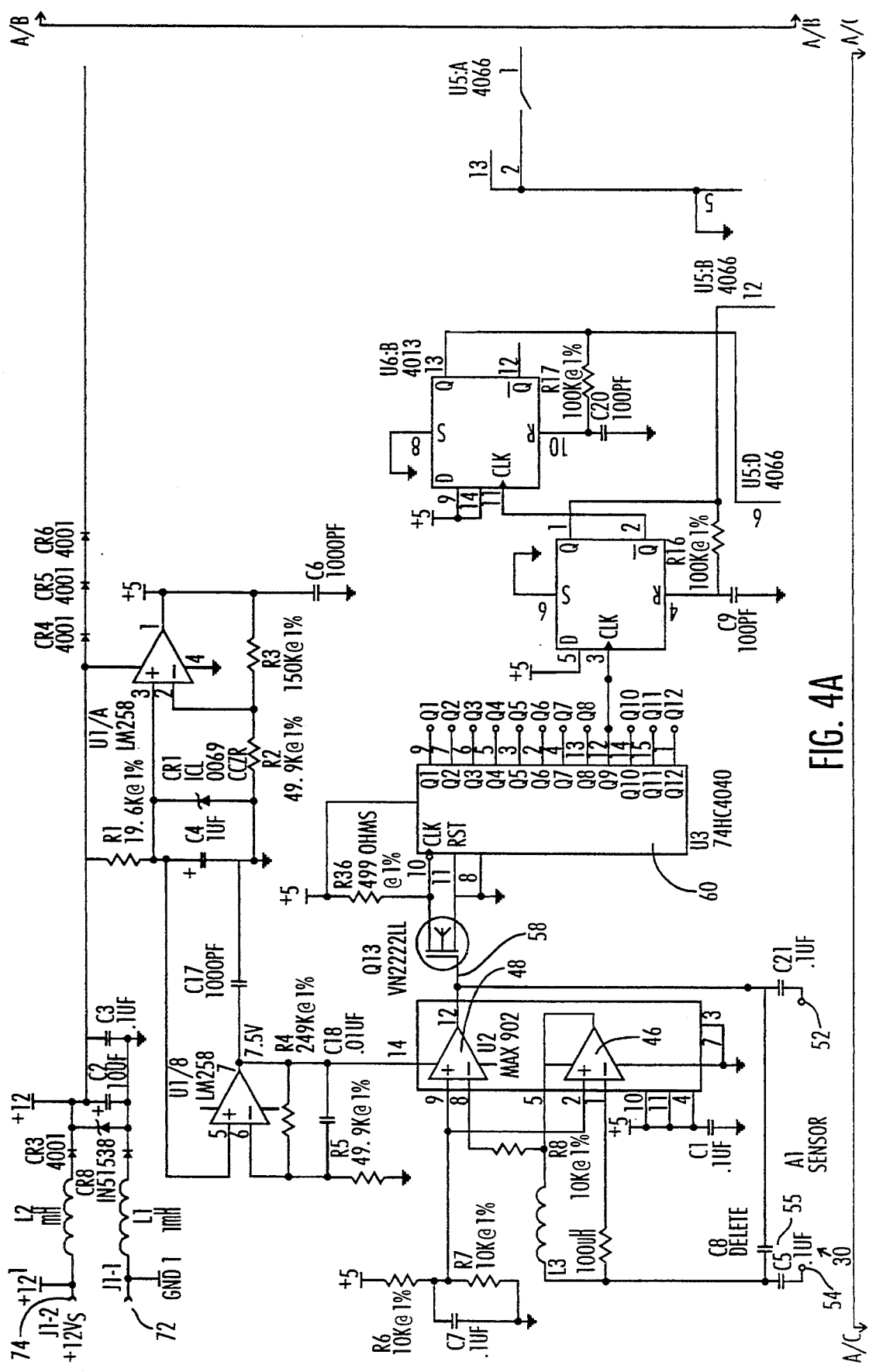
FIG. 4 is a schematic circuit diagram of a preferred embodiment of the electrical circuit on the printed circuit board of the soil moisture sensor of FIG. 1.
Figure 4B:
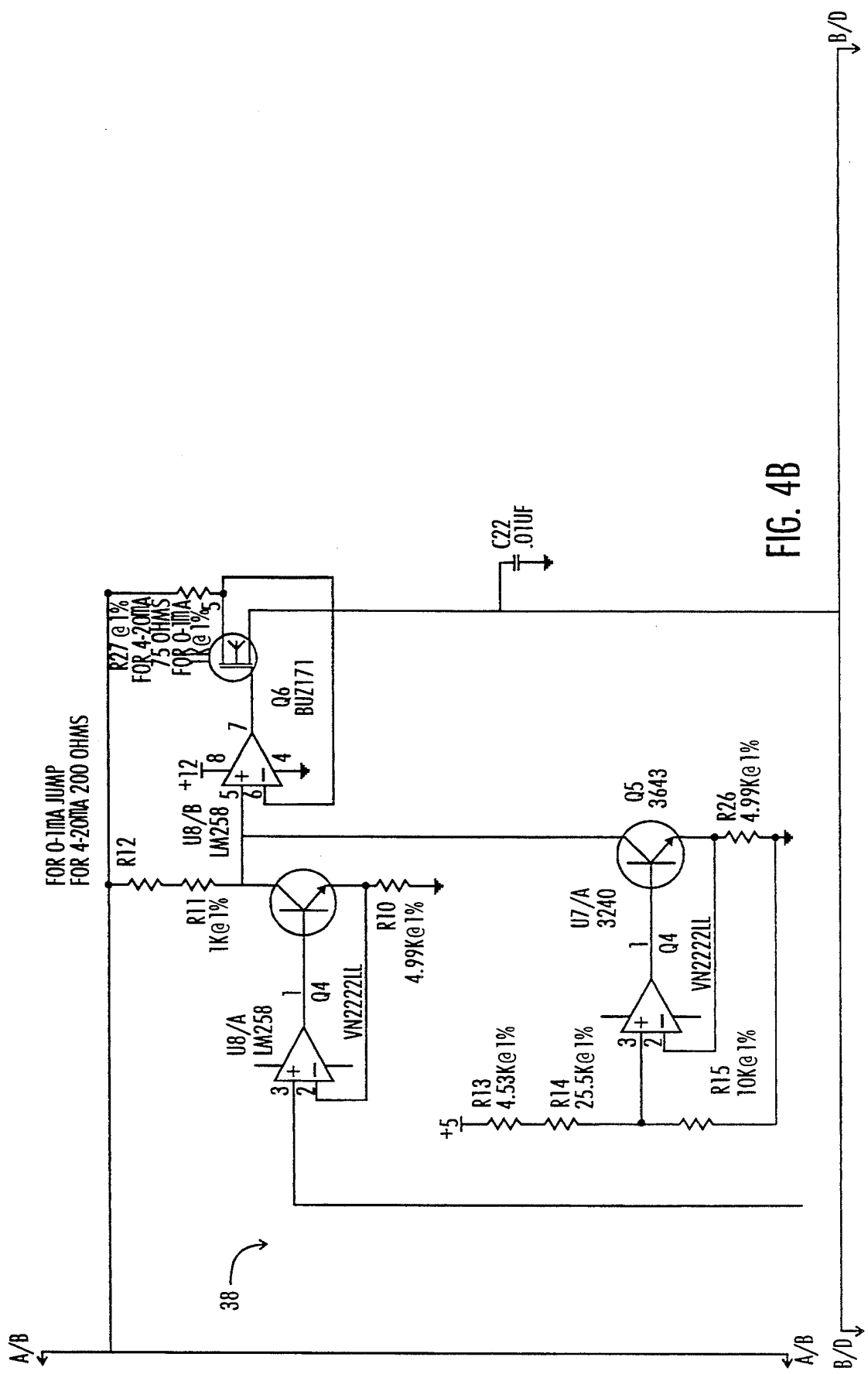
Figure 4C:
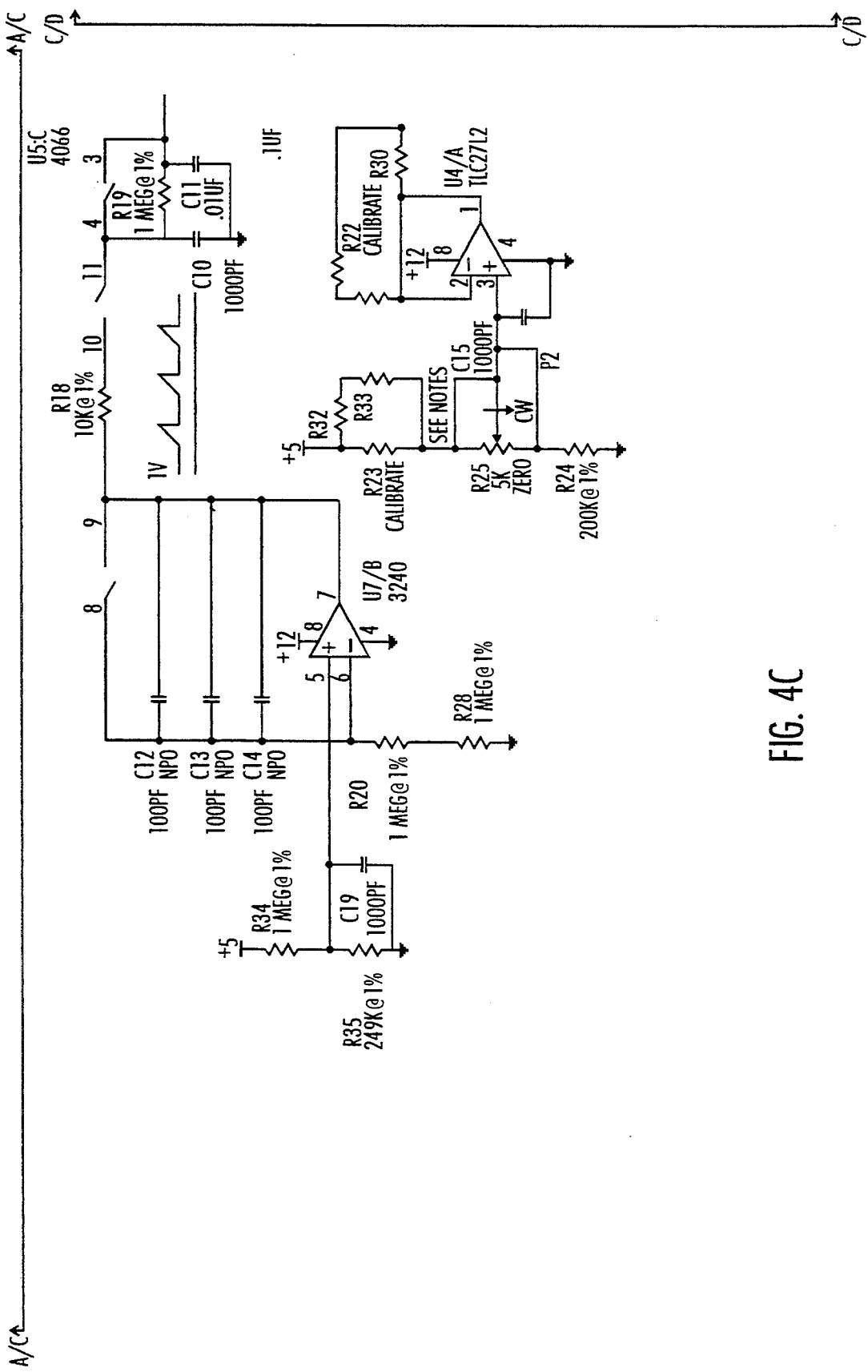
Figure 4D:
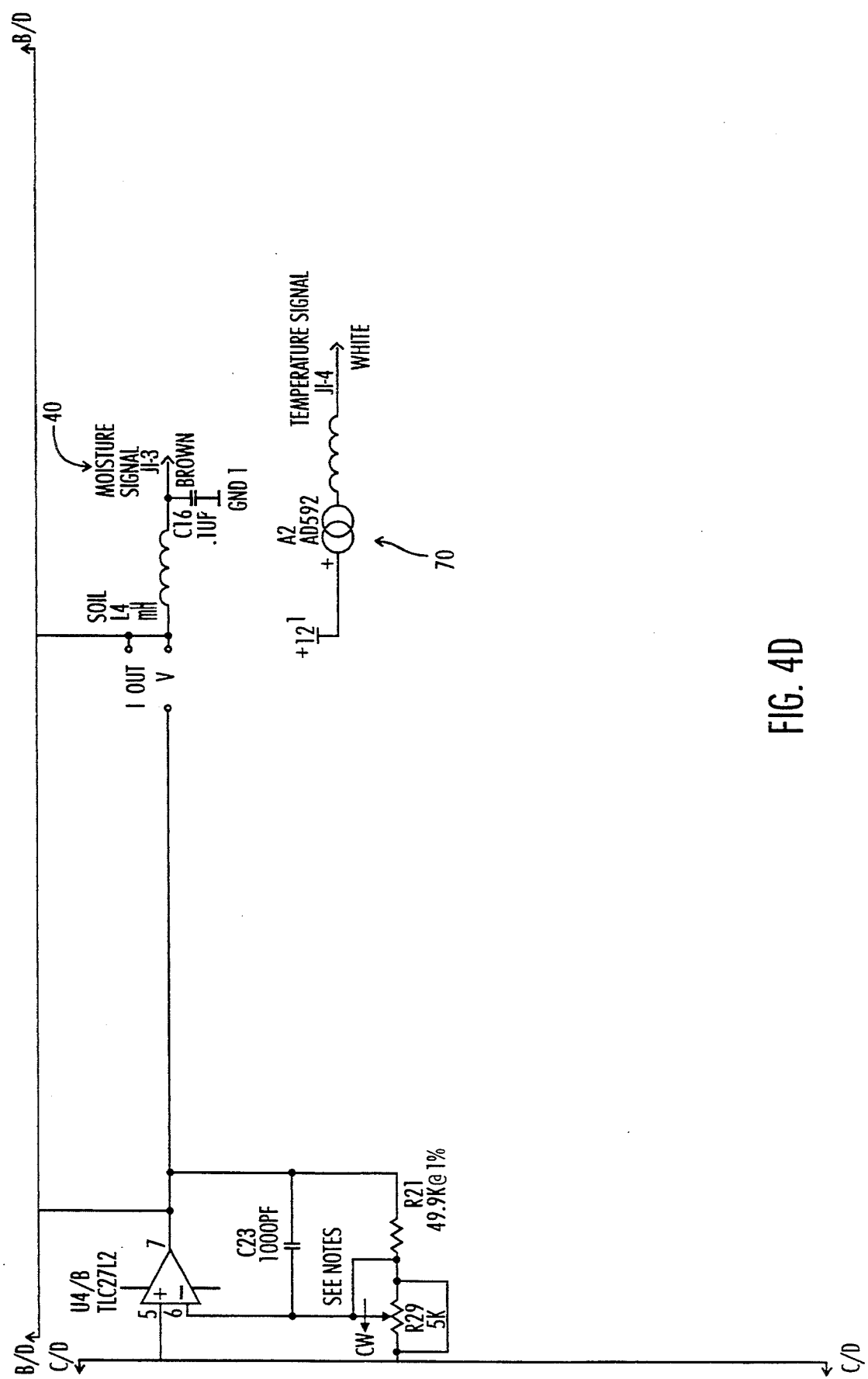

The following detailed description is of the best presently contemplated mode of carrying out the invention. This description is not to be taken in a limiting sense, but is made merely for the purpose of illustrating the general principles of embodiments of the invention. The scope of the invention is best defined by the appended claims.

The present invention relates generally to moisture sensor devices, systems and methods of making and using the same. In preferred embodiments, a moisture sensor device has a pair of elongated probe-like sensor elements which are installed (inserted or otherwise disposed) in a medium to be monitored. In general, the sensor elements and the medium at and around the installation location provide a capacitance value dependent upon the dielectric constant of the medium at and around the installation location. An electronic circuit coupled to the sensor elements provides an output electrical signal representative of the capacitance value and, thus, the dielectric constant of the medium at and around the installation location. Because water is the primary contributor to the dielectric constant of many mediums (such as soil), the electrical signal output of the electronic circuit is also representative of the moisture content of the medium at or around the installation location.

FIGS. 1 and 2 show a moisture sensor device 10 according to a preferred embodiment of the present invention. The sensor device 10 includes, in general, a pair of elongated sensor elements 12 and 13 coupled to an electronic module 14. The sensor elements 12 and 13 are spaced apart from each other by a gap 16. In preferred embodiments the width of the gap 16 is uniform along the length of the sensor elements 12 and 13.

In the illustrated embodiment, each sensor element 12 and 13 is composed of an elongated conductive probe having a rectangular cross-section (taken in the direction perpendicular to the longitudinal dimension L). In preferred embodiments, each probe has a pair of flat, planar sides (facing into and out of the page in FIG. 1) and a pair of relatively narrow sides (facing into or out of the page in FIG. 2). Examples of suitable dimensions for the width of each flat, planar side facing out of the page in FIG. 1 is approximately ½ inch, the width of each relatively narrow side facing out of the page in FIG. 2 is approximately 0.050 inch, and the width of the gap 16 is approximately ⅛ inch. These dimensions provide for a monitoring volume (the volume of medium being monitored) having a dimensions of a cylinder of approximately 3 inches in diameter and extending along the length of the sensor elements, as shown in broken lines in FIG. 2. Further embodiments may employ other suitable probe dimensions.

Because the probes are conductive over substantially their entire length, the capacitance provided by the probes and the medium at or around the installation location is averaged over the length of the probes. The length L of each probe is preferably determined based on the particular application of use of the sensor device. It has been found that a length dimension of approximately 29 inches is preferred for most applications. However, in further embodiments, the length L may be any suitable length. For example, sensor members configured for a small volume of medium (such as the soil around a potted plant) may be approximately 5 inches in length, whereas sensor members configured for more large scale operations may be 5 feet in length or longer.

Each conductive probe is preferably made of stainless steel. Other embodiments may employ other suitable conductive materials, such as brass, steel or copper (preferably plated with a suitable corrosion resistant material, such as chrome or nickel). However, stainless steel is preferred for its durability and corrosion resistance, as well as for ease of manufacture, cost efficiency and electrical sensitivity (especially if uncoated).

First and second braces 18 and 20, respectively, couple the end and mid sections of the respective sensor elements 12 and 13 together. The braces 18 and 20 help maintain the width of the gap 16 uniform along the length of the sensor elements. In addition, the first brace 18 covers the free ends of the sensor elements 12 and 13 to protect the sensor ends from damage which might otherwise occur during the process of installing the device into the soil (or other medium) to be tested. Preferably, the braces 18 and 20 are made of an electrically insulating material, so as to avoid forming an electrically conductive path between the sensor elements 12 and 13.

The electronic module 14 comprises a housing 22 containing a circuit for providing an electrical signal representative of moisture content and, in additional embodiments, a further electrical signal representative of temperature. An embodiment of such a circuit is described in more detail below with reference to FIG. 3, which may be manufactured in the form of an electrical circuit board. Preferably, the housing 22 is made of a durable, water-tight weather resistant material, such as a high strength plastic, epoxy, or the like, for protecting the circuit board from environmental factors.

In preferred embodiments, a communication link couples the electronic circuit in the module 14 to a central computer or processing station. In the illustrated embodiment, the communication link comprises a four conductor electrical cable 24 extending from the end of the module 14 opposite to the end from which the sensor elements 12 and 13 are coupled. Further embodiments may employ other suitable communication links, such as, but not limited to, optical, radio, microwave, conductive wire or combinations thereof. In yet further embodiments, the electronic circuit in the module 14 is connected directly to an irrigation controller which automatically adjusts irrigation conditions based on the output signal of the electronic circuit. Alternatively, the electronic circuit may be connected to a relay which controls (e.g., turns on or off) one or more valves or other irrigation or drainage control device. In such alternative embodiments, a user activated control switch may be provided to allow the user to select the particular output signal value which is needed to activate the relay.

A block diagram of an embodiment of the electronic circuit board housed in housing 22 is shown in FIG. 3 and a more detailed schematic diagram of an embodiment of the electrical circuit is shown in FIG. 4. In general, the electronic circuit board comprises an LC oscillator circuit 30, a frequency-to-analog signal convertor 32, a power input and regulator circuit 34, a noise filter circuit 36, an output driver circuit 38 and a signal output circuit 40.

In preferred embodiments, the LC oscillator circuit 30 should operate in the range of approximately 10 kHz to 10 MHz and should apply, for example, a square wave signal across the sensor elements. The square wave signal preferably has fast rise and fall times (for example, approximately 2 nano-seconds). An embodiment of an LC oscillator circuit 30 suitable for such operation includes first and second comparators 46 and 48, respectively, an inductor 50 and a pair of terminals 52 and 54 to which the probe members are coupled. In the FIG. 4 embodiment, comparators 46 and 48 are provided on a single circuit chip U2 (which may be, for example, model MAX 902, manufactured by MAXIM). A capacitor 55 may be included to provide the oscillator circuit 30 with a base, or dry operating frequency. FIG. 4 shows several other electrical components (resistors and capacitors) the functions of which will be apparent to one of ordinary skill in the art. A more simplified representation of the basic components of the LC oscillator circuit is shown in FIG. 5.

Figure 5:
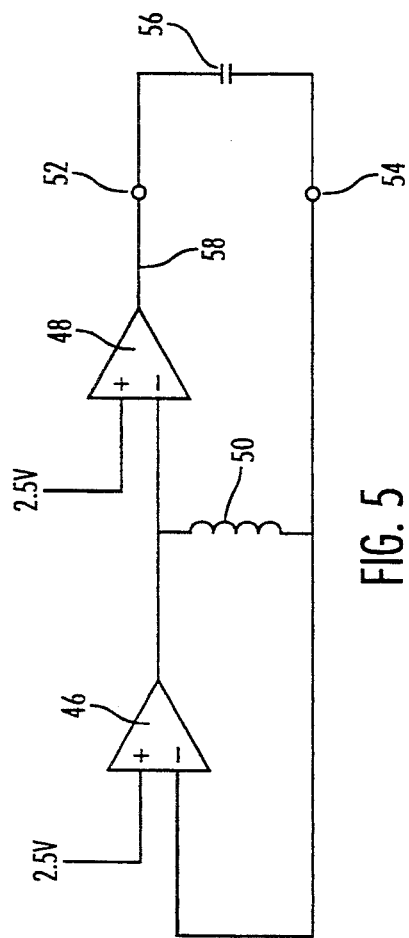
FIG. 5 is a generalized schematic circuit diagram of an LC oscillator circuit included in the circuit shown in FIGS. 3 and 4.

With reference to FIG. 5, a voltage signal (e.g., approximately 2.5 volts) is provided to the noninverting input of each comparator 46 and 48. The output of the first comparator 46 is coupled to the inverting input of the second comparator 48. The output of the second comparator 48 is coupled to terminal 52. Terminal 54 is coupled to the inverting input of the first comparator. A capacitor 56 represents the capacitance formed by the probe members and the material being monitored, as discussed in more detail below, and the parallel connected capacitor 55 (FIG. 4). The inductor 50 is coupled between the output and the inverting input of the first comparator 46. The LC oscillator circuit 30 defines a resonant frequency $f_0$ dependent on the value L of the inductor 50 and the value C of capacitor 56, based generally on the equation:

$$f_0 = 1/(2\pi \sqrt{LC})$$

With a predetermined, fixed inductance value L, the resonant frequency of the oscillator circuit 30 is dependent on the capacitance value C of capacitor 56. In this regard, the frequency of the signal output 58 of the second comparator 48 is dependent on the value of C of the capacitor 56. If the value of capacitor 55 is known in advance, then the component of the value C corresponding to the capacitance formed by the probe members and the material being monitored may be readily calculated.

As shown in FIG. 4, the frequency signal output 58 of the second comparator 48 (and, thus, the frequency signal output of the oscillator circuit 30) is coupled, through a level shifter, to the frequency-to-analog convertor circuit 32, wherein the frequency signal output of the oscillator circuit is converted to an analog signal having a magnitude dependent on the frequency of the oscillator circuit output signal. Because the frequency signal output of the oscillator may be relatively high, preferred embodiments of the frequency-to-analog convertor circuit 32 include a frequency divider circuit 60 for dividing the frequency signal prior to conversion.

The analog signal output 62 of the frequency-to-analog convertor circuit 32 has a voltage amplitude which is a function of the frequency of the oscillator output signal 58. A noise filter circuit 36 filters noise from the analog signal. The output driver circuit 38 provides an amplified voltage output signal 64 (having an amplitude dependent on the frequency of the oscillator output signal 58) to an output circuit 40, which provides the moisture sensor output signal 66 (also having an amplitude dependent on the frequency of the oscillator output signal 58 and, thus, dependent on the dielectric constant of the soil). In further embodiments, the electrical circuit provides an output signal in the form of a frequency signal (an electrical signal having a frequency dependent on the dielectric constant of the soil), e.g., to minimize the complexity and cost of the system. In yet further embodiments, a temperature sensor output signal 68 is provided by a conventional temperature sensor 70.

A power input and regulator circuit 34 has a ground terminal 72 and an input power signal terminal 74 to which a predetermined power input signal (such as a 12 Volt DC signal) is provided. The circuit 34 provides appropriate power signals to circuits 30, 32 and 38.

The four conductor cable 24 has a first conductor coupled to the power signal terminal 74, a second conductor coupled to the ground terminal 72, a third conductor coupled to the output of the output circuit 40 (for transmission of the moisture sensor output signal 66) and a fourth conductor coupled to the output of the temperature sensor 70 (for transmission of the temperature sensor output signal 68). Preferably, inductors are provided in the conduction path of the terminals 72 and 74, the output of circuit 40 and the output of the temperature sensor 70, as shown in FIG. 4 by inductors L1, L2, L4 and L5, respectively, for decoupling any parasitic capacitance between the earth and the module 14 or components of the communication link.

In further embodiments, an internal power source (e.g., battery, solar cells, or the like) may be provided in or adjacent the housing 22 so as to obviate the need for the first and second conductors of cable 24. In yet further embodiments, wireless transmission means (as discussed above) may be employed for transmission of the moisture sensor output signal 66 (and/or the temperature sensor output signal 68), obviating the need for the third (and fourth) conductor(s).

Figure 6:
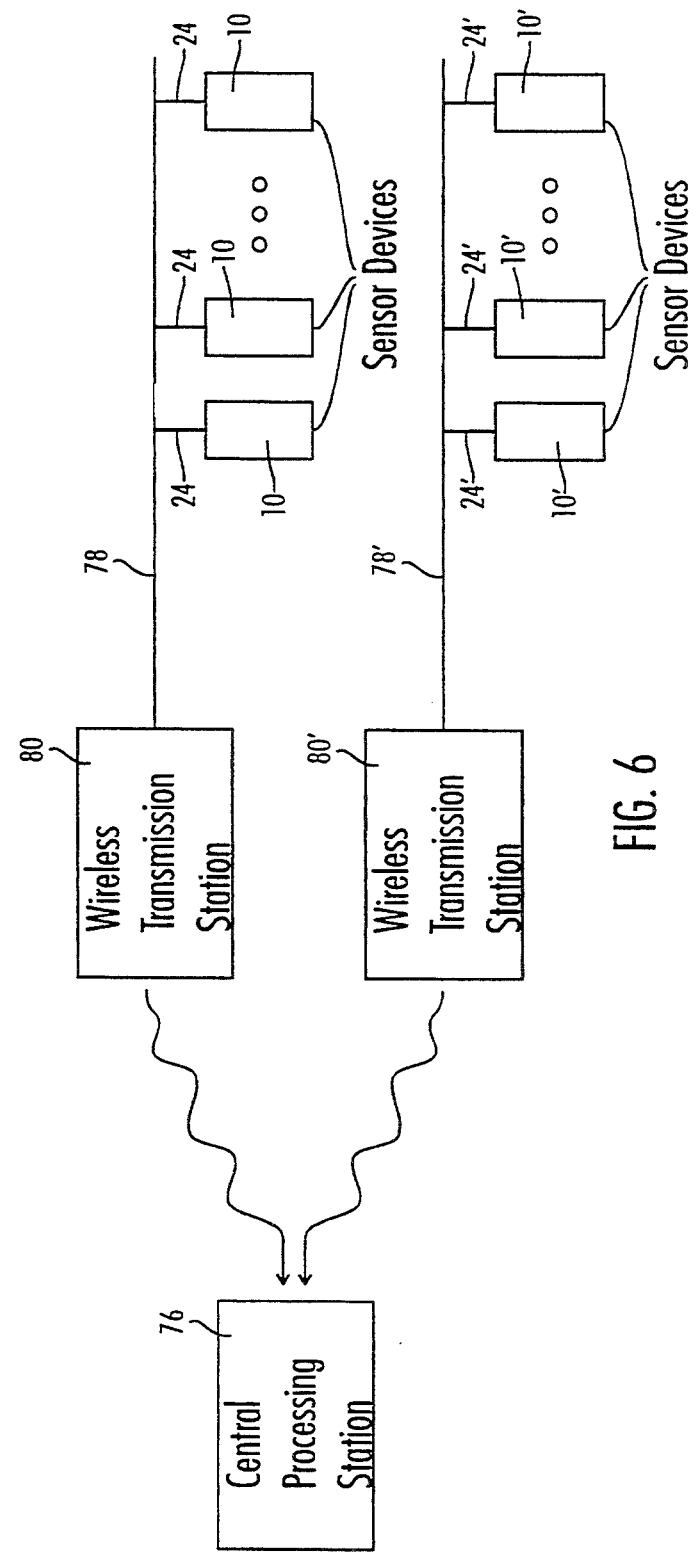
FIG. 6 is a block diagram of a moisture sensing system according to an embodiment of the present invention.

As noted above, it may be desirable to employ a plurality of moisture sensor devices 10 to monitor the moisture content of soil (or other medium) at a corresponding plurality of locations, as illustrated in the system shown in FIG. 6. For example, for agriculture applications, it may be desirable to monitor the moisture content of the soil in several locations in one or more agriculture fields, so that irrigation and/or drainage systems can be controlled in accordance with the actual soil moisture content. In such systems, it may be necessary to process the moisture sensor output signals (and possibly the temperature sensor output signals) of a plurality of moisture sensor devices. The moisture sensor output signals provide data from which suitable computing or processing equipment (e.g., located in at a central computer or processing station 76) process the data in accordance with well known data processing schemes. The data may be processed, for example, to make determinations regarding the control of irrigation channels, sprinkler systems, drainage channels, or the like.

In the FIG. 6 embodiment, data from a plurality of remote moisture sensor devices 10 are transmitted to the central processing station 76. The communication transmission link shown in FIG. 6 includes a cable 24 coupled to each sensor device 10 and a further cable or bus 78 coupling the cables 24 of a set of sensor devices 10 to a wireless signal transmitting station 80. The communication link also includes a wireless transmission link (such as a radio frequency, microwave, optical or other suitable link) between the transmission station 80 and the central processing station 76. In the FIG. 6 embodiment, a first plurality of sensor devices 10 are coupled to a first wireless transmission station 80, and a second plurality of sensor devices 10' are coupled to a second wireless transmission station 80'. Further sets (or pluralities) of sensor devices and associated wireless transmission stations may be employed in additional embodiments of the invention. In further embodiments, only one set of sensor devices and a corresponding wireless transmission station are employed. In yet further embodiments, the sensor devices are coupled directly to the central station (via wire or wireless links), obviating the need for a wireless transmission station 80 or 80'.

In the FIG. 6 embodiment, each sensor device 10 or 10' communicates with its respective wireless transmission station 80 or 80' and both wireless transmission stations 80 and 80' communicate with the central processing station 76 according to well known communication protocols (for example, but not limited to, time division multiplexing, discrete frequency or discrete polling schemes). In further embodiments, the wireless transmission link may be a two-way transmission link (e.g., wherein the station 76 and the station 80, or the sensors 10, each include a transceiver for transmitting and receiving communication signals) and the transmitting station 80 and/or the sensor devices 10 may include a resident processing device (such as a microprocessor) for controlling various operations in response to signals sent from the central station 76. In this manner, an operator (or operating program) at the central station 76 may remotely control, for example, the on-off state of various sensor devices 10.

In operation, one or more probe-like sensor elements are installed in a volume of the medium to be monitored (e.g., by pushing or burying the probe-like elements in the medium). As discussed above, the sensor elements have an elongated dimension (e.g., having a length of 29 inches) and function to provide an average capacitance over their length. In this regard, the sensor elements may be installed in a number of different angles or orientations so as to allow the installer to select the volume portion of the medium in which the average capacitance (and, thus, average moisture sensing) is to be provided.

For example, if the installer desires to sense the average moisture content of soil to a depth of about 29 inches, the installer should install the sensor elements in a generally vertical orientation, (or perpendicular to the soil surface) such that the sensor elements extend vertically downward to a depth of 29 inches. However, if the installer desires to sense the average moisture content of soil to a depth of 14 to 15 inches, the installer should install the sensor elements in a generally 45 degree orientation (relative to the soil surface), such that the sensor elements extend angularly downward to a depth of 14.5 inches. If the installer desires to sense the average moisture content to a very shallow depth, the sensor elements may be installed almost horizontally, near the surface of the medium. In this regard, sensor elements having a length of 29 inches can be used to sense the average moisture content in a medium, to a depth selectable from the range of almost 0 to approximately 29 inches. The user, therefore, has the ability to control the location, orientation and depth of the monitoring volume (the volume of medium being monitored, e.g., as shown in broken lines in FIG. 2). In this regard, the averaged moisture reading (averaged along the length of the sensor elements) is made over a user selected and controlled volume.

The sensor elements function as capacitor plates, while the medium between and around the sensor elements function as the capacitor dielectric. The capacitance C provided by the sensor elements and the medium is, therefore, dependent on the dielectric constant of the medium. The resonant frequency of the LC oscillator circuit is dependent, in part, on the value of the capacitance C and, therefore, on the dielectric constant of the medium. However, unlike typical RC oscillation circuits, the resistance of the medium (and, thus, the medium's conductivity) has minimal or no effect on the resonant frequency of an LC oscillator circuit, as discussed above.

The output signal of the LC oscillator circuit is converted to an analog signal having an amplitude dependent on the frequency of the oscillator circuit output signal and, thus, is dependent (and representative of) the dielectric constant of the medium. Because the conductivity of the medium has minimal effect on the resonant frequency of the LC oscillator circuit, the medium conductivity also has minimal effect on the amplitude of the analog signal. As a result, the amplitude of the analog signal provides a highly accurate indication of the dielectric constant of the medium (and, thus, the moisture content of the medium).

In a moisture sensor system as shown in FIG. 6, the cable or bus 78 receives an analog signal indicative of the dielectric constant of the medium in and around the installation location of each sensor device connected to the cable or bus. These analog signals are transmitted along the cable or bus 70 to the wireless transmission station 80, whereupon a wireless transmission signal (representative of each analog signal) is transmitted to the central processing station 76. At the central station 76, determinations may be made regarding the control of, for example, irrigation channels, sprinkler systems, drainage channels, or the like.

A further embodiment of the present invention provides both moisture sensing and conductivity sensing features, e.g., for detecting the concentration of saline (or other conductive material) in soil (or other medium). As noted above, some soils (or other media) have relatively high concentrations of conductive material (such as saline). However, the ability of such conductive materials to conduct a current through the soil (or other medium) depends on the moisture concentration of the soil (or other medium). That is, the concentration of moisture in the soil (or other medium) affects the conductivity of the soil (or other medium). Therefore, a conventional measurement of the conductivity of the soil (or other medium), in itself, would not provide meaningful information regarding the concentration of salts (or other conductive material) in the soil (or other medium) unless the moisture content of the soil (or other medium) were know. In this regard, a further preferred embodiment of the invention includes a moisture sensor (such as discussed above) as well as a conductivity sensor, e.g., combined into one sensing device, system or method. Suitable devices for sensing the conductivity of a medium (e.g., by passing a current through a medium) are well known in the art. An LC oscillator-based sensor, as discussed herein, provides an output signal representative of the dielectric property of the medium, with minimal or no dependance on the conductivity of the medium. Information regarding the moisture content (as obtained from the moisture sensor) is used to interpret information regarding the conductivity (as obtained from the conductivity sensor) such that a calculation of the concentration of salts (or other conductive material) in the soil (or other medium) is obtained, e.g., via suitable processing means, such as a microprocessor.

The invention may be embodied in other specific forms without departing from the spirit or central characteristics thereof. The present specification is therefore to be considered in all respects as illustrative and not restrictive, the scope of the invention being indicated by the appended claims rather than by the foregoing description, and all changes which come within the meaning and range of equivalency of the claims are to be embraced therein.

What is claimed is:

1. A method of sensing the moisture content of a volume of a medium, the medium having a dielectric constant dependant on the medium's moisture content, the method comprising the steps of:

disposing first and second spaced apart conductive sensor elements within said volume of the medium, to provide a capacitance dependent upon the dielectric constant of the medium when disposed within said volume of the medium;

coupling an inductance element to said first and second sensor elements in an LC oscillator circuit having an oscillation frequency dependent on the values of the inductance element and the capacitance value provided by the first and second sensor elements disposed in the medium; and outputting a moisture content indicative output signal as a function of the oscillation frequency of the LC oscillator circuit.

2. A method as recited in claim 1, further comprising the steps of:

transmitting an output signal having a signal characteristic dependent upon the oscillation frequency of the LC oscillator circuit;

monitoring the transmitted output signal at a processing station.

3. A method as recited in claim 1, wherein the step of disposing first and second spaced apart conductive sensor elements within said volume of the medium comprises the steps of:

selecting a volume of the medium in which an average moisture content is to be sensed, the selected volume having a generally cylindrical shape defining an axis extending at a selected angle relative to the surface of the medium and extending to a selected depth from the surface of the medium;

inserting first and second elongated, conductive probes, lengthwise into the selected volume and along the axis defined by the selected volume of the medium, wherein the probes define a capacitance value representative of the average capacitance along the length of probes when disposed within said volume of the medium.

4. A method of sensing the moisture content of a volume of a medium, the medium having a dielectric constant dependant on the medium's moisture content, the method comprising:

inducing oscillation in an LC oscillator circuit having an oscillation frequency dependent on the values of an inductance element and a capacitance element, the capacitance element comprising first and second spaced apart conductive sensor elements disposed within said volume of the medium, wherein the capacitance value provided by the first and second sensor elements is dependent upon the dielectric constant of the medium when the sensor elements are disposed within said volume of the medium; and outputting a moisture content indicative output signal as a function of the oscillation frequency of the LC oscillator circuit.

5. A moisture sensor device for sensing the moisture content of a volume of a medium, the medium having a dielectric constant dependant on the medium's moisture content, the device comprising:

an LC oscillator circuit having an inductance element and a capacitance element and an oscillation frequency dependent on the values of the inductance and capacitance elements;

wherein the capacitance element comprises first and second spaced apart conductive sensor elements configured to be disposed within said volume of the medium, to provide a capacitance dependent upon the dielectric constant of the medium when disposed within said volume of the medium; and an output circuit for providing a moisture content indicative output signal as a function of the oscillation frequency of the LC oscillator circuit.

6. A moisture sensor device as recited in claim 5, wherein each of the first and second conductive sensor elements comprises an elongated probe-like member.

7. A moisture sensor device as recited in claim 5, wherein each of the first and second conductive sensor elements comprises an elongated probe-like member having a length dimension of approximately 29 inches.

8. A moisture sensor device as recited in claim 5, wherein each of the first and second conductive sensor elements comprises an elongated probe-like member which is conductive along substantially its entire length such that, when disposed within said volume of the medium, the first and second sensor elements provide a capacitance value representative of the average capacitance along the length of the probe-like members.

9. A moisture sensor device as recited in claim 5, further comprising at least one brace coupling the first and second conductive sensor elements together.

10. A moisture sensor device as recited in claim 5, wherein each of the first and second conductive sensor elements comprises a stainless steel probe-like member.

11. A moisture sensor device as recited in claim 5, wherein each of the first and second conductive sensor elements comprises an elongated probe-like member having a longitudinal dimension and a generally rectangular cross-section shape taken in the direction perpendicular to the longitudinal dimension.

12. A moisture sensor device as recited in claim 5, wherein each of the first and second conductive sensor elements comprises an elongated probe-like member having a longitudinal dimension, a pair of generally flat, planar faces extending in the longitudinal direction, wherein the flat planar face of the first sensor element is arranged substantially coplanar with the flat, planar face of the second sensor element.

13. A moisture sensor device as recited in claim 5, wherein the LC oscillator circuit provides an output signal having a frequency dependent upon the oscillation frequency of the LC oscillator circuit, and wherein the output circuit comprises a frequency-to-analog convertor for providing an analog signal having an amplitude dependent on the frequency of the output signal of the LC oscillator circuit.

14. A moisture sensor device as recited in claim 12, further comprising an output terminal for providing an analog output signal having an amplitude dependent upon the oscillation frequency of the LC oscillator circuit.

15. A moisture sensor device as recited in claim 14, further comprising an inductor coupled to the output terminal for minimizing parasitic capacitance.

16. A moisture sensor device as recited in claim 5, wherein the LC oscillator circuit provides an output signal having a frequency dependent upon the oscillation frequency of the LC oscillator circuit, and the output circuit comprises:

a frequency-to-analog convertor for providing an analog signal having an amplitude dependent on the frequency of the output signal of the LC oscillator circuit;

an output driver for providing an output analog signal dependent on the analog signal provided by the frequency-to-analog convertor; and a power input and regulating circuit having a pair of input terminals for receiving an electrical potential signal thereacross.

17. A moisture sensor device as recited in claim 5, wherein the LC oscillator circuit provides an output signal having a frequency dependent upon the oscillation frequency of the LC oscillator circuit, and the output circuit comprises:

a frequency-to-analog convertor for providing an analog signal having an amplitude dependent on the frequency of the output signal of the LC oscillator circuit;

an output driver for providing an output analog signal dependent on the analog signal provided by the frequency-to-analog convertor;

a power input and regulating circuit having a pair of input terminals for receiving an electrical potential signal thereacross; and a temperature sensor for providing an electrical signal dependent on the temperature of the medium.

18. A moisture sensor device as recited in claim 5, wherein the LC oscillator circuit provides an output signal having a frequency dependent upon the oscillation frequency of the LC oscillator circuit, and the output circuit comprises:

a frequency-to-analog convertor for providing an analog signal having an amplitude dependent on the frequency of the output signal of the LC oscillator circuit;

an output driver for providing an output analog signal dependent on the analog signal provided by the frequency-to-analog convertor;

a power input and regulating circuit having a pair of input terminals for receiving an electrical potential signal thereacross;

a temperature sensor for providing an electrical signal dependent on the temperature of the medium;

a first electrical conductor coupled to receive the output analog signal of the output driver;

second and third electrical conductors respectively coupled to the pair of input terminals of the power input and regulating circuit; and a fourth electrical conductor coupled to receive the temperature dependent electrical signal provided by the temperature sensor.

19. A moisture sensor device as recited in claim 1, further comprising an output terminal for providing an output signal having a frequency dependent upon the oscillation frequency of the LC oscillator circuit.

20. A moisture sensor device as recited in claim 19, further comprising an inductor coupled to the output terminal for minimizing parasitic capacitance.

21. A moisture sensor device as recited in claim 5, wherein the LC oscillator circuit further comprises:

a first comparator having an inverting input terminal, a noninverting input terminal and an output terminal;

a second comparator having an inverting input terminal, a noninverting input terminal and an output terminal;

wherein the output terminal of the first comparator is coupled to the inverting input terminal of the second comparator, the inductance element is coupled between the output terminal and inverting input terminal of the first comparator and the capacitance element is coupled between the output terminal of the second comparator and the inverting input terminal of the first comparator.

22. A moisture sensor device as recited in claim 21, further comprising a power supply circuit for providing a voltage signal to the noninverting input terminals of the first and second comparators.

23. A moisture sensor system for sensing the moisture content of a medium, the medium having a dielectric constant dependant on the medium's moisture content, the system comprising:

at least one moisture sensor device having an LC oscillator circuit provided with an inductance element, a capacitance element and an oscillation frequency dependent on the values of the inductance and capacitance elements, wherein the capacitance element comprises first and second spaced apart conductive sensor elements configured to be disposed within said volume of the medium, to provide a capacitance dependent upon the dielectric constant of the medium when disposed within said volume of the medium;

an output circuit for providing a moisture content indicative output signal as a function of the oscillation frequency of the LC oscillator circuit; and a central processing unit for monitoring the output signal of the at least one moisture sensor.

24. A moisture sensor system as recited in claim 23, wherein said at least one moisture sensor device comprises a plurality of moisture sensor devices.

25. A moisture sensor system as recited in claim 20, further comprising a communication link means coupling said plurality of moisture sensor devices to said central processing unit.

26. A moisture sensor system as recited in claim 25, wherein the communication link includes a plurality of conductors and a corresponding plurality of inductors, each inductor being coupled to a respective one of said conductors for minimizing parasitic capacitance.

27. A moisture sensor system as recited in claim 25, wherein the communication link means comprises a wireless communication link means.

28. A moisture and conductivity sensor device for sensing the moisture content and conductivity of a volume of a medium, the medium having a dielectric constant dependant on the medium's moisture content and a conductivity dependent on the medium's moisture content and the concentration of conductive material in the medium, the device comprising:

an LC oscillator circuit having an inductance element and a capacitance element and an oscillation frequency dependent on the values of the inductance and capacitance elements;

wherein the capacitance element comprises first and second spaced apart conductive sensor elements configured to be disposed within said volume of the medium, to provide a capacitance dependent upon the dielectric constant of the medium when disposed within said volume of the medium;

a conductivity sensor for sensing the conductivity of the medium with said volume:

means responsive to the sensed conductivity of the medium within said volume and further responsive to the oscillation frequency of the LC oscillator circuit, for providing a signal representative of the component of the sensed conductivity contributed by the concentration of conductive material in said volume of the medium.

* * * * *